US008992980B2

(12) United States Patent
Henke et al.

(10) Patent No.: US 8,992,980 B2
(45) Date of Patent: Mar. 31, 2015

(54) WATER-SOLUBLE MELOXICAM GRANULES

(75) Inventors: Stefan Henke, Gau-Odernheim (DE); Martin Andreas Folger, Ingelheim (DE); Jens Schmalz, Hueffelsheim (DE); Diana Christine Keilhofer, Mainz (DE); Hans-Juergen Kroff, Schoeneberg (DE); Nina Herz, Windesheim (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 900 days.

(21) Appl. No.: 10/694,569

(22) Filed: Oct. 27, 2003

(65) Prior Publication Data
US 2004/0180092 A1 Sep. 16, 2004

Related U.S. Application Data

(60) Provisional application No. 60/508,184, filed on Oct. 2, 2003.

(30) Foreign Application Priority Data

Oct. 25, 2002 (DE) .................................. 102 50 081

(51) Int. Cl.
A61K 31/5415 (2006.01)
A61K 9/00 (2006.01)
A61K 9/16 (2006.01)
A61K 9/50 (2006.01)

(52) U.S. Cl.
CPC ............. *A61K 9/5078* (2013.01); *A61K 9/0095* (2013.01); *A61K 9/1617* (2013.01); *A61K 31/5415* (2013.01); *A61K 9/5089* (2013.01)
USPC ........................................ 424/489; 514/226.5

(58) Field of Classification Search
CPC ............ A61K 31/5412; A61K 9/0095; A61K 9/1617; A61K 9/5089
See application file for complete search history.

(56) References Cited

U.S. PATENT DOCUMENTS

| 2,795,529 | A | | 6/1957 | Alburn et al. |
| 3,288,675 | A | | 11/1966 | Newmark et al. |
| 3,849,549 | A | | 11/1974 | Dempski et al. |
| 3,931,212 | A | | 1/1976 | Satzinger et al. |
| 3,947,576 | A | | 3/1976 | Kuczkowski et al. |
| 4,233,299 | A | | 11/1980 | Trummlitz et al. |
| 4,482,554 | A | | 11/1984 | Gebhardt et al. |
| 4,628,053 | A | | 12/1986 | Fries |
| 4,702,919 | A | | 10/1987 | Kitamori et al. |
| 4,748,174 | A | | 5/1988 | Veronesi |
| 4,794,117 | A | | 12/1988 | Corbiere |
| 4,835,187 | A | | 5/1989 | Reuter et al. |
| 4,942,167 | A | | 7/1990 | Chiesi et al. |
| 5,169,847 | A | | 12/1992 | Nagy nee Kricsfalussy et al. |
| 5,178,878 | A | * | 1/1993 | Wehling et al. ............ 424/466 |
| 5,283,065 | A | | 2/1994 | Doyon et al. |
| 5,304,561 | A | | 4/1994 | Sarfarazi |
| 5,360,611 | A | | 11/1994 | Robertson et al. |
| 5,414,011 | A | | 5/1995 | Fu et al. |
| 5,464,632 | A | | 11/1995 | Cousin et al. |
| 5,489,439 | A | | 2/1996 | Bola |
| 5,556,639 | A | | 9/1996 | Fielden |
| 5,654,003 | A | | 8/1997 | Fuisz et al. |
| 5,700,816 | A | | 12/1997 | Isakson et al. |
| 5,811,446 | A | | 9/1998 | Thomas |
| 5,824,658 | A | | 10/1998 | Falk et al. |
| 5,886,030 | A | | 3/1999 | Maniar |
| 6,046,191 | A | | 4/2000 | Hamley et al. |
| 6,071,539 | A | * | 6/2000 | Robinson et al. ............ 424/466 |
| 6,106,862 | A | | 8/2000 | Chen et al. |
| 6,136,804 | A | | 10/2000 | Nichtberger |
| 6,166,012 | A | | 12/2000 | Muller et al. |
| 6,180,136 | B1 | | 1/2001 | Larson et al. |
| 6,183,779 | B1 | * | 2/2001 | Ouali et al. ............ 424/472 |
| 6,184,220 | B1 | | 2/2001 | Turck et al. |
| 6,187,800 | B1 | | 2/2001 | Suri et al. |
| 6,221,377 | B1 | | 4/2001 | Meyer |
| 6,284,269 | B1 | * | 9/2001 | Struengmann et al. ....... 424/461 |
| 6,319,519 | B2 | | 11/2001 | Woolfe et al. |
| 6,495,603 | B1 | | 12/2002 | Miyake et al. |
| 6,550,955 | B2 | | 4/2003 | D'Silva |

(Continued)

FOREIGN PATENT DOCUMENTS

| AU | 673675 B2 | 11/1996 |
| CA | 1102802 | 6/1981 |

(Continued)

OTHER PUBLICATIONS

Parkh, Handbook of Pharmaceutical Granulation Technology, first edition, 1997, Marcel Dekker, 59-67.*
Dow Chemicals Brochure, entitled "Using METHOCEL cellulose ethers for controlled release of drugs in hyrophilic matrix systems." Publication Jul. 2000, Form No. 198-02075-700 AMS, pp. 1-36.
Hydrated Silica webpage, Kosmix Corporation, Apr. 21, 2011, pp. 1-14.
Saha et al., "Effect of solubilizing excipients on permeation of poorly water-soluble compounds across Caco-2 cell monolayers". European Journal of Pharmaceutics and Biopharmaceutics, vol. 50, No. 3, 2000, pp. 403-411, Abstract accessed at http://cat.inist.fr/?aModele=afficheN&cpsidt=798854, accessed on Aug. 13, 2010, 3 pages.

(Continued)

*Primary Examiner* — Kyle Purdy
(74) *Attorney, Agent, or Firm* — Michael P. Morris; Joyce L. Morrison

(57) ABSTRACT

Water soluble meloxicam granules comprising:
(a) meloxicam;
(b) a salt forming agent which forms the meglumine, sodium, potassium, or ammonium salt of meloxicam;
(c) a binder;
(d) a sugar or sweetener; and
(e) a carrier,
and optionally a flavoring agent and optionally other excipients, processes for preparing them and their use for treating respiratory or inflammatory complaints in mammals.

28 Claims, No Drawings

(56) References Cited

U.S. PATENT DOCUMENTS

| | | | |
|---|---|---|---|
| 6,599,529 B1* | 7/2003 | Skinhøj et al. | 424/458 |
| 6,605,295 B1 | 8/2003 | Bellmann et al. | |
| 6,630,056 B1 | 10/2003 | Thibierge et al. | |
| 6,669,957 B1 | 12/2003 | Laruelle et al. | |
| 6,682,747 B1 | 1/2004 | Turck et al. | |
| 6,869,948 B1* | 3/2005 | Bock et al. | 514/226.5 |
| 6,986,346 B2 | 1/2006 | Hochrainer et al. | |
| 7,105,512 B2 | 9/2006 | Morizono et al. | |
| 7,969,206 B2 | 6/2011 | Ito | |
| 2001/0055569 A1 | 12/2001 | Davis et al. | |
| 2002/0006440 A1 | 1/2002 | Cherukuri | |
| 2002/0016342 A1 | 2/2002 | Scolnick et al. | |
| 2002/0035107 A1 | 3/2002 | Henke et al. | |
| 2002/0068088 A1 | 6/2002 | Gruber | |
| 2002/0077328 A1 | 6/2002 | Hassan et al. | |
| 2002/0099049 A1 | 7/2002 | Burch et al. | |
| 2002/0106345 A1 | 8/2002 | Uhrich et al. | |
| 2002/0187187 A1* | 12/2002 | Ohki et al. | 424/465 |
| 2003/0050305 A1 | 3/2003 | Tejada | |
| 2003/0055051 A1 | 3/2003 | Morizono et al. | |
| 2003/0109701 A1 | 6/2003 | Coppi et al. | |
| 2003/0119825 A1 | 6/2003 | Folger et al. | |
| 2003/0199482 A1 | 10/2003 | Seibert et al. | |
| 2003/0220306 A1 | 11/2003 | Simmons et al. | |
| 2004/0001883 A1 | 1/2004 | Matsui et al. | |
| 2004/0024041 A1 | 2/2004 | Selzer | |
| 2004/0024042 A1 | 2/2004 | Breyer | |
| 2004/0037869 A1 | 2/2004 | Cleverly et al. | |
| 2004/0043992 A1 | 3/2004 | Tolba et al. | |
| 2004/0110747 A1 | 6/2004 | Altman | |
| 2004/0170687 A1 | 9/2004 | Hurd et al. | |
| 2004/0171611 A1 | 9/2004 | Trummlitz et al. | |
| 2004/0180092 A1 | 9/2004 | Henke et al. | |
| 2004/0198826 A1 | 10/2004 | Baiker et al. | |
| 2004/0204413 A1* | 10/2004 | Faour et al. | 514/248 |
| 2004/0204472 A1 | 10/2004 | Briggs et al. | |
| 2004/0214753 A1 | 10/2004 | Britten et al. | |
| 2004/0229038 A1 | 11/2004 | Cooper et al. | |
| 2004/0234596 A1 | 11/2004 | Ohki et al. | |
| 2004/0253312 A1 | 12/2004 | Sowden et al. | |
| 2005/0038018 A1 | 2/2005 | Kanbe et al. | |
| 2005/0147664 A1 | 7/2005 | Liversidge et al. | |
| 2005/0187212 A1 | 8/2005 | Ohki et al. | |
| 2005/0187213 A1 | 8/2005 | Lang et al. | |
| 2005/0197332 A1 | 9/2005 | Altman | |
| 2005/0244491 A1 | 11/2005 | Ohki et al. | |
| 2005/0245510 A1 | 11/2005 | Friton et al. | |
| 2005/0277634 A1 | 12/2005 | Janott et al. | |
| 2005/0288280 A1 | 12/2005 | Friton et al. | |
| 2006/0079516 A1 | 4/2006 | Henke et al. | |
| 2006/0160793 A1 | 7/2006 | Altman | |
| 2006/0217431 A1 | 9/2006 | Daemmgen et al. | |
| 2007/0077296 A1 | 4/2007 | Folger et al. | |
| 2007/0099907 A1 | 5/2007 | Altman | |
| 2008/0132493 A1 | 6/2008 | Folger et al. | |
| 2008/0234380 A1 | 9/2008 | Shapiro | |
| 2008/0280840 A1 | 11/2008 | Lang et al. | |
| 2011/0083985 A1 | 4/2011 | Folger et al. | |
| 2011/0275618 A1 | 11/2011 | Folger et al. | |
| 2012/0077764 A1 | 3/2012 | Freehauf et al. | |
| 2013/0178467 A1 | 7/2013 | Henke et al. | |
| 2014/0066440 A1 | 3/2014 | Folger et al. | |
| 2014/0113893 A1 | 4/2014 | Folger et al. | |

FOREIGN PATENT DOCUMENTS

| | | |
|---|---|---|
| CA | 2164100 A1 | 1/1995 |
| CA | 2166204 A1 | 1/1995 |
| CA | 2326517 A1 | 10/1999 |
| CA | 2404360 A1 | 9/2001 |
| CA | 2414063 A1 | 12/2001 |
| CA | 2469588 | 6/2003 |
| CA | 2503396 A1 | 5/2004 |
| DE | 3434707 A1 | 4/1985 |
| DE | 3700172 A1 | 7/1987 |
| DE | 4217971 C1 | 10/1993 |
| DE | 19729879 A1 | 1/1999 |
| DE | 10010123 A1 | 9/2001 |
| DE | 10024752 A1 | 11/2001 |
| DE | 10032132 A1 | 1/2002 |
| DE | 10300323 A1 | 10/2004 |
| EP | 0002482 A1 | 6/1979 |
| EP | 0034432 A2 | 8/1981 |
| EP | 0093999 A2 | 11/1983 |
| EP | 0177870 A2 | 4/1986 |
| EP | 0179430 A2 | 4/1986 |
| EP | 0298192 A1 | 1/1989 |
| EP | 0306984 A1 | 3/1989 |
| EP | 0360246 A1 | 3/1990 |
| EP | 0390071 A1 | 10/1990 |
| EP | 0422681 A1 | 4/1991 |
| EP | 0465235 A1 | 1/1992 |
| EP | 0560329 A1 | 9/1993 |
| EP | 0945134 A1 | 9/1999 |
| EP | 1082966 | 3/2001 |
| EP | 1190714 A2 | 3/2002 |
| EP | 1568369 A1 | 8/2005 |
| ES | 2065846 A1 | 2/1995 |
| ES | 2159564 T3 | 10/2001 |
| FR | 2437838 A1 | 4/1980 |
| GB | 2455875 A | 6/2009 |
| IT | 1251650 B | 5/1995 |
| JP | 47007352 Y1 | 3/1972 |
| JP | S52102416 A | 8/1977 |
| JP | 56191118 A | 5/1986 |
| JP | 1299230 A | 12/1989 |
| JP | H06157312 A | 6/1994 |
| JP | H0912426 A | 1/1997 |
| JP | 11139971 A | 5/1999 |
| JP | 2001170083 A | 6/2001 |
| JP | 2003535902 A | 12/2003 |
| JP | 3550782 B2 | 8/2004 |
| JP | 4018022 B2 | 12/2007 |
| JP | 04321624 B2 | 8/2009 |
| WO | 9301814 A1 | 2/1993 |
| WO | 9400420 A1 | 1/1994 |
| WO | 9509639 A1 | 4/1995 |
| WO | 9517178 A1 | 6/1995 |
| WO | 9518604 A1 | 7/1995 |
| WO | 9603387 A1 | 2/1996 |
| WO | 9603388 A1 | 2/1996 |
| WO | 9610999 A2 | 4/1996 |
| WO | 9611192 A1 | 4/1996 |
| WO | 9641625 A1 | 12/1996 |
| WO | 9703655 A1 | 2/1997 |
| WO | 9703667 A1 | 2/1997 |
| WO | 9717978 A1 | 5/1997 |
| WO | 9717989 A1 | 5/1997 |
| WO | 9729776 A1 | 8/1997 |
| WO | 9731631 A1 | 9/1997 |
| WO | 9817250 A1 | 4/1998 |
| WO | 9909988 A1 | 3/1999 |
| WO | 9912524 A1 | 3/1999 |
| WO | 9927906 A1 | 6/1999 |
| WO | 9939730 A1 | 8/1999 |
| WO | 9949845 A1 | 10/1999 |
| WO | 9949867 A1 | 10/1999 |
| WO | 9955320 A1 | 11/1999 |
| WO | 9959634 A1 | 11/1999 |
| WO | 0015195 A1 | 3/2000 |
| WO | 0108689 A1 | 2/2001 |
| WO | 0137838 A1 | 5/2001 |
| WO | 0152897 A2 | 7/2001 |
| WO | 0187343 A2 | 11/2001 |
| WO | WO 01/97813 A2 | 12/2001 |
| WO | 02085331 A1 | 10/2002 |
| WO | 03049733 A1 | 6/2003 |
| WO | 03082297 A1 | 10/2003 |
| WO | 03097066 A1 | 11/2003 |
| WO | 2004004776 A1 | 1/2004 |
| WO | 2004026116 A2 | 4/2004 |
| WO | 2004026313 A1 | 4/2004 |
| WO | 2004037264 A1 | 5/2004 |

(56) References Cited

FOREIGN PATENT DOCUMENTS

| | | | |
|---|---|---|---|
| WO | 2004089379 A2 | 10/2004 | |
| WO | 2004103283 A2 | 12/2004 | |
| WO | 2005002542 A2 | 1/2005 | |
| WO | 2005004915 A2 | 1/2005 | |
| WO | 2005079806 A1 | 9/2005 | |
| WO | 2005105101 | 11/2005 | |
| WO | 2005115386 A1 | 12/2005 | |
| WO | 2006000306 A1 | 1/2006 | |
| WO | 2006100213 A1 | 9/2006 | |
| WO | 2007039417 A1 | 4/2007 | |
| WO | 2007135505 A2 | 11/2007 | |
| WO | 2008113149 A2 | 9/2008 | |
| WO | 2011107498 A1 | 9/2011 | |
| WO | 2011138197 A2 | 11/2011 | |

OTHER PUBLICATIONS

Schneeweis et al., "In Vivo and In Vitro Diclofenac Sodium Evaluation After Rectal Application of Soft Gelatine Capsules Enabling Application Induced Transformation (AIT) into a Seminsolid System of Liquid Crystals (SSLC) for Controlled Release". Pharmaceutical Research, vol. 14, No. 12, Dec. 1997, pp. 1726-1729.

Sciencelab.com, "Lactose, Monohydrate, Spray-Dried Powder, NF". Accessed at http://www.epoxy-paint.net/page/.S/PVAR/10419/SLL1453, Feb. 29, 2008, 2 pages.

Sorbera et al., "Lumiracoxib Antiarthritic, COX-2 Inhibitor". Drugs of the Future, vol. 27, No. 8, Aug. 2002, pp. 740-747.

Stei et al., "Local Tissue Tolerability of Meloxicam, a New NSAID: Indications for Parental, Dermal and Mucosal Administration". British Journal of Rheumatology, vol. 35, Supp. 1, 1996, pp. 44-50.

Straus et al., "New Evidence for Stroke Prevention: Clinical Applications". The Journal of the American Medical Association, vol. 288, No. 11, Sep. 2002, pp. 1396-1398.

Straus et al., "New Evidence for Stroke Prevention: Scientific Review". The Journal of the American Medical Association, vol. 288, No. 11, Sep. 2002, pp. 1388-1395.

Sunose et al., "The Effect of Cyclooxygenase 2 Inhibitor, FK3311, on Ischemia-Reperfusion Injury in Canine Lung Transplantation". Journal of Heart and Lung Transplantation, vol. 19, No. 1, Jan. 2000, p. 40.

Tuerck et al., "Clinical Pharmacokinetics of Meloxicam". Arzneimittel-Forschung, vol. 47, No. 3, 1997, pp. 253-258.

Tunuguntla et al., "Management of Prostatitis". Prostate Cancer and Prostatic Diseases, vol. 5, No. 3, 2002, pp. 172-179.

Vippagunta et al., "Crystalline solids". Advanced Drug Delivery Reviews, vol. 48, 2001, pp. 3-26.

Wagenlehner et al., "Therapy of Prostatitis Syndrome". Der Urologe [A], vol. 40, No. 1, pp. 24-28.

Gunew et al., "Long-term safety, efficacy and palatability of oral meloxicam at 0.01-0.03 mg/kg for treatment of osteoarthritic pain in cats". Journal of Feline Medicine and Surgery, vol. 10, 2008, pp. 235-241.

"Committee for Veterinary Medicinal Products—Meloxicam (Extension to Pigs)—Summary Report (5)". The European Agency for the Evaluation of Medicinal Products, Veterinary Medicines and Information Technology, Dec. 2000, pp. 1-3.

"Metacam (R) 0.5 mg/ml oral suspension for cats." Boehringer Ingelheim Datasheet, Web site: http://www.vetgb.com/vetgb_pdfs/metacamc_7a5c_vetgb.pdf> Accessed on Jun. 8, 2010.

"Metacam(R)" FDA Animal & Veterinary Drug Labels, Web site: http://www.fda.gov/downloads/AnimalVeterinary/Products/ApprovedAnimalDrugProducts/DrugLabels/UCM050397.pdf> Accessed Jun. 8, 2010.

"Metacam—Community register of veterinary medicinal products" accessed online at http://pharmacos.eudra.org/F2/register/v004.htm.

"Types of Solutions". University of Wisconsin, Stevens Point, Feb. 1, 2001, accessed at http://www.uwsp.edu/chemistry/tzamis/chem106pdfs/solutionexamples.pdf, Google date sheet included, 2 pages.

Abstract in English of DE10024752, 2001.
Abstract in English of FR2437838, 1980.
Abstract in English of JP47007352, 1972.
Abstract in English of DE3434707, 1985.
Abstract in English of JP02906528, 1999.
Abstract in English of JP11139971, 1999.

Altman et al., "Efficacy Assessment of Meloxicam, a Preferential Cyclooxygenase-2 Inhibitor, in Acute Coronary Syndromes Without ST-Segment Elevation: The Nonsteroidal Anti-Inflammatory Drugs in Unstable Angina Treatment-2 (NUT-2) Pilot Study". Circulation, vol. 106, 2002, pp. 191-195.

Ansel et al., "Pharmaceutical Dosage Forms and Drug Delivery Systems". Seventh Edition, Lippincott Williams & Wilkins, Philadelphia, PA, 1999, pp. 77-87.

Bednarek et al., "Effect of steroidal and non-steroidal anti-imflammatory drugs in combination with long-acting oxytetracycline on non-specific immunity of calves suffering from enzootic bronchopneumonia". Veterinary Microbiology, vol. 96, 2003, pp. 53-67.

Bednarek et al., "The effect of steroidal and non-steroidal anti-inflammatory drugs on the cellular immunity of calves with experimentally-induced local lung inflammation". Veterinary Immunology and Immunopathology, vol. 71, 1999, pp. 1-15.

Boehringer Ingelheim; Metacam (Meloxicam) Now Approved for Pigs and Mastitis in Dairy Cows; May 2003 Press Release; pp. 1-2.

Cho et al., "In vitro effects of *Actinobacillus pleuropneumoniae* on inducible nitric oxide synthase and cyclooxygenase-2 in porcine alveolar macrophages". American Journal of Veterinary Research, vol. 64, No. 12, Dec. 2003, pp. 1514-1518.

D'Yakov et al., "Long term use of Tamsulosin (omnic®) in Patients with Chronic Prostatitis". Urologiia, vol. 5, 2002, pp. 10-12.

Del Tacca et al., "Efficacy and Tolerability of Meloxicam, a COX-2 Preferential Nonsteroidal Anti-Inflammatory Drug". Clinical Drug Investigation, vol. 22, No. 12, 2002, pp. 799-818.

Dellabella et al., "Conservative Managment of Juxtavesical Calculi with Tamsulosin". European Urology Supplements, Vol. 2, No. 1, 2003, p. 81.

Dunn et al., "Tamsulosin: A Review of its Pharmacology and Therapeutic Efficacy in the Management of Lower Urinary Tract Symptoms". Drugs & Aging, vol. 19, No. 2, 2002, pp. 132-161.

Engelhardt et al., "Meloxicam: Influence on Arachidonic Acid Metabolism". Biochemical Pharmacology, vol. 51, 1996, pp. 21-28.

Ettmayer et al., "Lessons Learned from Marketed and Investigational Prodrugs". Journal of Medicinal Chemistry, vol. 47, No. 10, May 2004, pp. 2393-2404.

European Search Report for EP10155400 dated Jun. 9, 2010.
European Search Report for EP10162015 dated Aug. 30, 2010.

Farkouh et al., "Comparison of lumiracoxib with naproxen and ibuprofen in the Therapeutic Arthritis Research and Gastrointestinal Event Trial (TARGET), cardiovascular outcomes: randomised controlled trial". Lancet, vol. 364, Aug. 2004, pp. 675-684.

Fitzgerald et al., "COX-2 inhibitors and the cardiovascular system". Clinical and Experimental Rheumatology, vol. 19, No. 6, Supp. 25, Nov. 2001, pp. S31-S36.

Fitzpatrick et al., "Recognising and Controlling Pain and Inflammation in Mastitis". Proceedings of the British Mastitis Conference, Axient/Institute for Animal Health, Milk Development Council/Novartis Animal Health, 1998, pp. 36-44.

Giuliani et al., "Role of Antithrombotic Therapy in Cardiac Disease". Mayo Clinic Practice of Cardiology, Third Edition, Mosby, St. Louis, MO, 1996, pp. 1116-1121.

Gollackner et al., "Increased apoptosis of hepatocyctes in vascular occulusion after orthotopic liver transplantation". Transplant International, vol. 13, No. 1, 2000, pp. 49-53.

Gruet et al., "Bovine mastitis and intramammary drug delivery: review and perspectives". Advanced Drug Delivery Reviews, vol. 50, 2001, pp. 245-259.

Guth et al., "Pharmacokinetics and pharmacodynamics of terbogrel, a combined thromboxane A2 receptor and synthase inhibitor, in healthy subjects". British Journal of Clinical Pharmacology, vol. 58, No. 1, Jul. 2004, pp. 40-51.

Hawkey et al., "Gastrointestinal Tolerability of Meloxicam Compared to Diclofenac in Osteoarthritis Patients". British Journal of Rheumatology, vol. 37, No. 9, 1998, pp. 937-945.

(56) References Cited

OTHER PUBLICATIONS

Hirsch et al, "Investigation on the efficacy of meloxicam in sows with mastitis-metritis-agalactia syndrome". Journal of Veterinary Pharmacology and Therapeutics, vol. 26, 2003, pp. 355-360.
http://dictionary.reference.com/search?q=ambient.
International Preliminary Examination Report for PCT/EP2003/011802 completed Feb. 1, 2005.
International Search Report and Written Opinion for PCT/EP2003/011802 mailed Feb. 3, 2004. [Please see International Preliminary Examination Report for translation of Written Opinion.].
Jain et al., "Antiplatelet therapy in acute coronary syndromes without persistent ST-segment elevation". Cardiovascular Drugs and Therapy, vol. 15, No. 5, Sep. 2001, pp. 423-436. [Abstract Only].
Kimura et al., "Effect of cilostazol on platelet agrregation and experimental thrombosis". Arzneimittel-Forschung, vol. 35, No. 7A, 1985, pp. 1144-1149. [Abstract Only].
Kumar et al., "Comparative Studies on Effect of Some Hydrophilic Polymers on the Dissolution Rate of a Poorly Water Soluble Drug, Meloxicam". Indian Drugs, vol. 39, No. 6, Apr. 2002, pp. 323-329.
Lieberman et al., "Tablet Formulation and Design" in Pharmaceutical Dosage Forms: Tablets, vol. 1, Second Edition, Marcel Dekker, Inc., New York, New York, 1989, pp. 105-108.
Luger et al., "Structure and physicochemical properties of meloxicam, a new NSAID". European Journal of Pharmaceutical Sciences, vol. 5, 1996, pp. 175-187.
Macdonald Campus of McGill University, "Mastitis in Dairy Cows", published online, Jul. 2003, pp. 1-12.
McDonald et al., "Calpain inhibitor I reduces the activation of nuclear factor-KappaB and Organ Injury/Dysfunction in Hemorrhagic Shock". The FASEB Journal, vol. 15, Jan. 2001, pp. 171-186.
Noble et al., "Meloxicam". Drugs, vol. 51, No. 3, Mar. 1996, pp. 424-430.
Physicians' Desk Reference, 55th Edition, Medical Economics Company, Inc., 2001, pp. 981-984 and pp. 1404-1406.
Rantanen et al., "Process Analysis of Fluidized Bed Granulation". AAPS PharmsciTech, vol. 2, No. 4, Article 21, 2001, 8 pages.
Remington: The Science and Practice of Pharmacy, 19th Edition, vol. II, Mack Publishing Company, Easton, Pennsylvania, 1995, p. 1646.
Robson et al., "Intrinsic acute renal failure (ARF) associated with non-steroidal anti-inflammatory drug (NSAId) use in juvenile cats undergoing routine desexing—16 cases 1998-2005". May 2006, Journal of Veterinary Internal Medicine, vol. 20, No. 3, Abst. 109, p. 740.
Rudnic et al., "Oral Solid Dosage Forms".,Gennaro, Editior, Remington's Pharmaceutical Sciences, 18th Edition, Mack Publishing Company, Easton, PA, 1990, pp. 1633-1645 and pp. 1654-1655.
Abstract in English of JP2001170083, 2001.
Abstract in English of JP4018022, 2007.
Abstract in English of JP3550782, 2004.
Abstract in English of WO199301814, 1993.
Chemical Abstracts, vol. 118, No. 18, Abstract No. 175803, XP002087682, 1993, 1 page.
Abstract in English of ES2065846, 1995.
Gerritsen et al., "Prostaglandin Synthesis and Release from Cultured Human Trabecular-meshwork Cells and Scleral Fibroblasts". Experimental Eye Research, vol. 43, No. 6, 1986, pp. 1089-1102.
Herbort et al., "Anti-inflammatory Effect of Topical Diclofenac After Argon Laser Trabeculoplasty: Preliminary Results of a Placebo Controlled Study". Klin. Monatsbl. Augenheik, vol. 200, No. 5, May 1992, pp. 358-361.
Pharma Projects, Dialog File 928, Accession Nr. 0021312, Diclofenac, InSite Vision, 1996, 5 pages.
Snyder et al., "Corticosteroid Treatment and Trabecular Meshwork Proteases in Cell and Organ Culture Supernatants". Experimental Eye Research, vol. 57, No. 4, 1993, pp. 461-468.
Masferrer et al., "Cyclooxygenase-2 Inhibitors: A New Approach to the Therapy of Ocular Inflammation". Survey of Ophthalmology, vol. 41, Supp. 2, Feb. 1997, pp. S35-S40.
Abstract in English for IT1251650, 1995.
Li et al., "Degradation mechanism and kinetic studies of a novel anticancer agent, AG2034". International Journal of Pharmaceutics, vol. 167, 1998, pp. 49-56.
Bunji, Kouho, "Tissue Damage Due to Infections". Drug Injection Handbook, Fundamentals of Blending Variation for Injection Drugs, Nanzando Co. Ltd., Tokyo, 1976, p. 5.
Pharmaceutical Excipent Encyclopedia, Yakuji Nippo Ltd., Tokyo, 1994, pp. 2-5.
Nell et al., "Comparison of vedaprofen and meloxicam in dogs with muskuloskeletal pain and inflammation". Journal of Small Animal Practice, vol. 43, No. 5, May 2002, pp. 208-212 [Accessed at http://www.ncbi.nlm.nih.gov/pubmed/12038853 on Sep. 27, 2013]. Abstract Only, 1 page.
Abstract in English for JPH06157312, 1994.
Abstract in English of WO1999039730, 1999.
Ansel et al., "Dosage Form Design: Pharmaceutic and Formulation Considerations". Pharmaceutical Dosage Forms and Drug Delivery Systems, Seventh Edition, Lippincott Williams & Wilkins, Philadelphia, PA, 1999, pp. 66 and pp. 89.

\* cited by examiner

WATER-SOLUBLE MELOXICAM GRANULES

RELATED APPLICATIONS

This application claims benefit of U.S. Ser. No. 60/508,184, filed Oct. 2, 2003, and claims priority to German Application No. 102 50 081.9, filed Oct. 25, 2002, each of which is hereby incorporated by reference in its entirety.

FIELD OF THE INVENTION

The present invention relates to meloxicam granules which dissolve rapidly in water, containing meloxicam, a salt forming agent which forms the meglumine, sodium, potassium, or ammonium salt of meloxicam, binders, a sugar or sweetener, a carrier, optionally a flavoring, and optionally other excipients, processes for preparing them, and their use for treating respiratory or inflammatory complaints in mammals.

BACKGROUND OF THE INVENTION

Meloxicam (4-hydroxy-2-methyl-N-(5-methyl-2-thiazolyl)-2H-1,2-benzothiazine-3-carboxamide-1,1-dioxide) is an active substance which belongs to the group of NSAIDs (non-steroidal-antiinflammatory drugs). Meloxicam and the sodium and meglumine (N-methyl-D-glucamine) salt thereof are described in EP-A-0 002 482. EP-A-0 945 134 discloses the pH-dependent solubility characteristics of meloxicam and its salts, i.e., the sodium salt, the ammonium salt, and the meglumine salt, in aqueous solution. According to this, meloxicam is an active substance which does not dissolve readily in water. The meloxicam salts, particularly the meglumine salt, exhibit improved solubility as the pH increases between 4 and 10, as shown in Table 1 of EP-A-0 945 134.

It is known that administering medicaments to sick animals, particularly those suffering from fever, can be done particularly easily and successively through their drinking water. Administering to their food can also make it easier to give the medicament to the animal. It is known from EP-A-0 945 134 that meloxicam and meglumine cannot easily be compressed. The aim of the present invention is therefore to develop a granulated form of meloxicam which can be administered to the animals by mixing it into their drinking water or as a food supplement.

DESCRIPTION OF THE INVENTION

Surprisingly, meloxicam granules have been discovered which can easily be produced by a fluidized bed method and which, when dissolved in water, form a drinking water solution which is stable over at least 48 hours. It was also found that these granules can be added to the animals' food.

The invention therefore relates to water soluble granules containing meloxicam, a salt forming agent which forms the meglumine, sodium, potassium, or ammonium salt of meloxicam, binders, a sugar or sweetener, a carrier, optionally a flavoring, and optionally other excipients.

The meloxicam granules according to the invention have a number of advantages over existing preparations.

In sick animals, an increased uptake of drinking water can be observed when a drink containing meloxicam is given. Suitable dilution of the dissolved granules allows a variable, precise dosing of the active substance meloxicam. Because of the good solubility of the meloxicam granules according to the invention in water, the effects of meloxicam in the body of the sick animal set in very rapidly. The good flavor of the meloxicam granules also makes it possible to administer them as a food supplement. In addition, the granules according to the invention have very good flow properties, a uniform meloxicam content, they are virtually free from dust and have a narrow particle size distribution of 125 µm to 500 µm. The total solubility of the granules in water ensures optical control of a totally dissolved active substance which is only available for therapeutic use in this form when administered in drinking water. In a preferred embodiment of the invention, the salt forming agent is meglumine. In another preferred embodiment of the invention, the binder may be selected from among hydroxypropylmethylcellulose, polyvinylpyrrolidone, gelatine, starch, and polyethylene glycol ether, preferably hydroxypropylmethylcellulose, polyvinylpyrrolidone, and polyethylene glycol ether, most preferably hydroxypropylmethylcellulose and polyvinylpyrrolidone.

In another preferred embodiment of the invention, the sugar or sweetener may be selected from among sodium saccharine, aspartame, and SUNETT® sweetener (acesulfame potassium, preferably sodium saccharine or aspartame. Particularly preferred according to the invention are meloxicam granules in which the flavoring is selected from among vanilla, honey flavoring, apple flavoring, and contramarum, preferably honey flavoring and apple flavoring. Also particularly preferred are meloxicam granules in which the carrier is selected from among lactose, glucose, mannitol, xylitol, sucrose, and sorbitol, preferably glucose, lactose, or sorbitol, more preferably glucose or lactose, most preferably glucose.

Particularly preferred are meloxicam granules in which the content of meloxicam is between 0.05% and 4%, preferably between 0.1% and 2%, preferably between 0.3% and 1.5%, more preferably between 0.4% and 1%, most preferably 0.6%. Also particularly preferred are meloxicam granules which contain meglumine and meloxicam in a molar ratio of about 9:8 to 12:8, preferably 10:8.

The invention further relates to process for preparing the meloxicam granules according to the invention in which the steps (a) to (c) are carried out successively:

(a) preparing an aqueous granulating liquid containing binder, optionally a sugar or sweetener, meloxicam, meglumine, and/or a flavoring;
(b) spraying the granulating liquid on to a carrier in a topspray fluidized bed method with an air current supplied at a constant temperature from 50° C. to 80° C., preferably 65° C.; and
(c) a subsequent coating process with an aqueous granulating liquid by the topspray fluidized bed method containing a binder, a sugar or sweetener, and/or a flavoring.

In a preferred process according to the invention the granulating liquid is prepared by stirring and heating the components to 70° C. to 100° C., preferably about 90° C.

A particular feature of the meloxicam granules according to the invention is that they have a long term stability of 24 months or more when stored in their original package at room temperature.

A particularly preferred granulated meloxicam preparation contains meloxicam, meglumine, hydroxypropylmethylcellulose, povidone, and glucose monohydrate.

The present invention further relates to the use of meloxicam granules for preparing a pharmaceutical composition for treating pain, inflammation, fever, acute mastitis, diarrhea, lameness, problems of mobility, and respiratory complaints in animals, preferably acute mastitis, diarrhea, lameness, mobility problems, and respiratory complaints, preferably acute mastitis, diarrhea, lameness, mobility problems, and respiratory complaints, most preferably mobility problems or respiratory complaints. The treatment may be given in conjunction with antibiotic treatment.

The formulation according to the invention is suitable for treating animals, preferably mammals, particularly domestic pets or farm animals, such as pigs, horses, cattle, dogs, or cats, preferably pigs or horses.

The meloxicam granules according to the invention are preferably used in amounts corresponding to a dosage range from 0.2 to 1.0 mg of active substance per kg of bodyweight, preferably 0.4 to 0.8 mg/kg of bodyweight, preferably 0.5 to 0.7 mg/kg of bodyweight, more preferably 0.6 mg/kg of bodyweight.

It is also preferable to use the meloxicam granules according to the invention to prepare a pharmaceutical composition which can be administered both in drink and also as a feed supplement.

The formulation according to the invention may contain, as the meloxicam salt, the meglumine, sodium, potassium or ammonium salt, preferably the meloxicam meglumine salt.

The proportion of meglumine is between 0.035% and 2.8%, preferably 0.07% to 1.4%, preferably 0.21% to 1.05%, more preferably 0.28% to 0.7%, particularly about 0.42% in the meloxicam granules. The possible concentrations of sodium, potassium, and ammonium may be calculated accordingly.

The concentration of the binder may be in the range from 20 mg/g to 80 mg/g, preferably 30 mg/g to 70 mg/g, preferably 40 mg/g to 60 mg/g, most preferably 50 mg/g of granules.

The concentration of the sugar may be in the range from 50 mg/g to 150 mg/g, preferably 75 mg/g to 125 mg/g, more preferably about 100 mg/g of granules.

The concentration of the sweetener may be in the range from 1 mg/g to 10 mg/g, preferably 2 mg/g to 5 mg/g, more preferably about 3 mg/g of granules.

The concentration of the carrier may be in the range from 800 mg/g to 985 mg/g, preferably 900 mg/g to 960 mg/g, more preferably about 930 mg/g of granules.

The concentration of the flavoring may be in the range from 0.1 mg/g to 10 mg/g, preferably 0.2 mg/g to 1.0 mg/g, more preferably about 0.5 mg/g of granules.

The packaging material used for the formulation according to the invention may be any of a number of standard commercial materials for granules. These include, for example, plastic containers, e.g., made of HPPE (high pressure polyethylene), aluminum bags, or paper bags with an aluminum lining.

The meloxicam granules are produced by the top spray fluidized bed method. In this, first of all an aqueous granulating liquid solution consisting of about 50 to 70 g/kg of binder, such as PVP 25000, hydroxypropylmethylcellulose or Macrogol 6000, preferably hydroxypropylmethylcellulose, and/or about 1 to 5 g/kg of sweeteners such as SUNETT® sweetener (acesulfame potassium) or Na saccharine, preferably SUNETT® sweetener (acesulfame potassium), and/or about 0.5 to 2.5 g of flavoring, such as vanilla, honey, flavoring 203180, or contramarum, preferably honey, about 10 g to 15 g of meloxicam (peg milled) and about 7 g to 11 g of meglumine is produced with stirring by heating to about 70° C. to 100° C.

The granulating liquid is then sprayed on to a carrier such as lactose, glucose, or sorbitol, preferably glucose, by a counter flow process (top spray process). This is done, for example, using a two-component nozzle, spraying at a constant air pressure at about 50° C. to 80° C., preferably at about 65° C. The coating process may then be carried out using a second aqueous granulating liquid. In order to prepare a solution ready for use, a stock solution should be dissolved completely in water. Then the stock solution may be adjusted to the desired concentration for use by mixing with water. To increase safety in use, the granules may have water soluble color markings.

The meloxicam granules according to the invention will be illustrated by the examples that follow. The skilled person will be aware that these examples are intended solely as an illustration and should not be regarded as limiting the invention.

Example 1

0.6% Meloxicam Granules

| Recipe: | g/100 g |
|---|---|
| Meloxicam | 0.6 |
| Meglumine | 0.42 |
| Hydroxypropylmethylcellulose | 3.00 |
| Povidone | 2.00 |
| Glucose monohydrate | 93.98 |

Example 2

1.2% Meloxicam Granules

| Meloxicam | 1.2 |
|---|---|
| Meglumine | 0.84 |
| Hydroxypropylmethylcellulose | 3.00 |
| Collidone 25 | 2.0 |
| Glucose Monohydrate | 92.96 |

Example 3

0.6% Meloxicam Granules

| Meloxicam | 0.6 |
|---|---|
| Meglumine | 0.42 |
| Pharmacoat 606 | 4.0 |
| Macrogol 6000 | 1.0 |
| Acesulfame K | 0.3 |
| Lactose | 93.68 |

Example 4

0.6% Meloxicam Granules

| Meloxicam | 0.6 |
|---|---|
| Meglumine | 0.42 |
| Pharmacoat 606 | 4.75 |
| Macrogol 6000 | 0.25 |
| Acesulfame K | 0.3 |
| Liquid vanilla flavoring | 0.05 |
| Lactose | 93.63 |

Bright yellow free flowing meloxicam granules corresponding to Examples 1 to 4 may be prepared as follows:

The granules are stored for 3 months at 25° C. at a relative humidity of 60%. No significant changes were observed in terms of the active substance content, the water content (according to Karl-Fischer), the visual solubility characteristics, the pH in demineralized water, and the visual wetability. In order to determine the visual solubility characteristics, 5 g of the granules were dissolved in 100 mL of demineralized water at ambient temperature. After about 1 minute, a clear yellowish solution was obtained.

We claim:

1. Water soluble granules consisting of:
   (a) meloxicam;
   (b) a salt forming agent which forms the meglumine, sodium, potassium, or ammonium salt of meloxicam;
   (c) a binder;
   (d) a sugar or sweetener; and
   (e) a carrier,
   and optionally a flavoring agent;
   wherein 5 g of said granules dissolve in 100 mL of demineralized water in about 1 minute to form a clear solution, and the water soluble granules do not include cyclodextrin.

2. The water soluble meloxicam granules according to claim 1, wherein the salt forming agent is meglumine.

3. The water soluble meloxicam granules according to claim 1, wherein the binder is selected from hydroxypropylmethylcellulose, polyvinylpyrrolidone, gelatine, starch, or polyethylene glycol ether.

4. The water soluble meloxicam granules according to claim 2, wherein the binder is selected from hydroxypropylmethylcellulose, polyvinylpyrrolidone, gelatine, starch, or polyethylene glycol ether.

5. The water soluble meloxicam granules according to claim 1, wherein the sugar or sweetener is selected from sodium saccharine, aspartame, and acesulfame potassium.

6. The water soluble meloxicam granules according to claim 2, wherein the sugar or sweetener is selected from sodium saccharine, aspartame, and acesulfame potassium.

7. The water soluble meloxicam granules according to claim 3, wherein the sugar or sweetener is selected from sodium saccharine, aspartame, and acesulfame potassium.

8. The water soluble meloxicam granules according to claim 4, wherein the sugar or sweetener is selected from sodium saccharine, aspartame, and acesulfame potassium.

9. The water soluble meloxicam granules according to claim 1, wherein the flavoring agent is selected from vanilla, honey flavoring, apple flavoring, or contramarum.

10. The water soluble meloxicam granules according to claim 2, wherein the flavoring agent is selected from vanilla, honey flavoring, apple flavoring, or contramarum.

11. The water soluble meloxicam granules according to claim 3, wherein the flavoring agent is selected from vanilla, honey flavoring, apple flavoring, or contramarum.

12. The water soluble meloxicam granules according to claim 4, wherein the flavoring agent is selected from vanilla, honey flavoring, apple flavoring, or contramarum.

13. The water soluble meloxicam granules according to claim 1, wherein the carrier is selected from lactose, glucose, mannitol, xylitol, sucrose, and sorbitol.

14. The water soluble meloxicam granules according to claim 2, wherein the carrier is selected from lactose, glucose, mannitol, xylitol, sucrose, and sorbitol.

15. The water soluble meloxicam granules according to claim 3, wherein the carrier is selected from lactose, glucose, mannitol, xylitol, sucrose, and sorbitol.

16. The water soluble meloxicam granules according to claim 4, wherein the carrier is selected from lactose, glucose, mannitol, xylitol, sucrose, and sorbitol.

17. The water soluble meloxicam granules according to claim 1, wherein the proportion of meloxicam is between 0.05% and 4%.

18. The water soluble meloxicam granules according to claim 2, wherein the molar ratio of meglumine to meloxicam is 9:8 to 12:8.

19. The water soluble meloxicam granules according to claim 2, wherein the molar ratio of meglumine to meloxicam is about 10:8.

20. Water soluble granules consisting of meloxicam, meglumine, hydroxypropylmethylcellulose, povidone, and glucose monohydrate.

21. A process for preparing the water soluble meloxicam granules according to claim 1, the process comprising:
    (a) preparing an aqueous granulating liquid containing the binder, the sugar or sweetener, the meloxicam, the salt forming agent, and/or the flavoring agent;
    (b) spraying the granulating liquid on to a carrier in a topspray fluidized bed method with a supply of air at a constant temperature of 50° C. to 80° C.; and
    (c) performing a coating process with an aqueous granulating liquid by the topspray fluidized bed method containing the binder, the sugar or sweetener, and/or the flavoring agent.

22. A process for preparing the water soluble meloxicam granules according to claim 2, the process comprising:
    (a) preparing an aqueous granulating liquid containing the binder, the sugar or sweetener, the meloxicam, the meglumine, and/or the flavoring agent;
    (b) spraying the granulating liquid on to a carrier in a topspray fluidized bed method with a supply of air at a constant temperature of 50° C. to 80° C.; and
    (c) performing a coating process with an aqueous granulating liquid by the topspray fluidized bed method containing the binder, the sugar or sweetener, and/or the flavoring agent.

23. The process according to claim 21, wherein the granulating liquid is prepared by stirring and heating the components to 70° C. to 100° C.

24. The process according to claim 22, wherein the granulating liquid is prepared by stirring and heating the components to 70° C. to 100° C.

25. The water soluble granules according to claim 1, wherein
    the binder is present in an amount of about 2 to about 8 percent;
    the sugar or sweetener is present in an amount of about 5 to 15 percent; and
    the carrier is present in an amount of about 80 to about 98 percent.

26. The water soluble meloxicam granules according to claim 1, wherein the granules have a particle size distribution of 125 µm to 500 µm.

27. The process according to claim 21, wherein the granules have a particle size distribution of 125 µm to 500 µm.

28. Water soluble granules consisting of:
    (a) meloxicam;
    (b) a salt forming agent which forms the meglumine, sodium, potassium, or ammonium salt of meloxicam;
    (c) a binder consisting of at least one of hydroxypropylmethylcellulose, polyvinylpyrrolidone, gelatine, starch, and polyethylene glycol ether;
    (d) a sugar or sweetener consisting of at least one of sodium saccharine, aspartame, and acesulfame potassium; and
    (e) a carrier consisting of at least one of lactose, glucose, mannitol, xylitol, sucrose, and sorbitol, and optionally a flavoring agent consisting of at least one of vanilla, honey flavoring, apple flavoring, and contramarum;

wherein 5 g of said granules dissolve in 100 mL of demineralized water in about 1 minute to form a clear solution.

* * * * *